United States Patent [19]

Harding

[11] Patent Number: 5,231,652

[45] Date of Patent: * Jul. 27, 1993

[54] ARRANGEMENT FOR MEASURING THE PULSE TRANSMISSION SPECTRUM OF X-RAY QUANTA

[75] Inventor: Geoffrey Harding, Hamburg, Fed. Rep. of Germany

[73] Assignee: U.S. Philips Corp., New York, N.Y.

[*] Notice: The portion of the term of this patent subsequent to Apr. 16, 2008 has been disclaimed.

[21] Appl. No.: 717,737

[22] Filed: Jun. 19, 1991

[30] Foreign Application Priority Data

Jun. 20, 1990 [DE]  Fed. Rep. of Germany ....... 4019613
Oct. 31, 1990 [DE]  Fed. Rep. of Germany ....... 4034602

[51] Int. Cl.$^5$ ........................................ G01N 23/201
[52] U.S. Cl. ...................................... 378/86; 378/88; 378/147; 378/149
[58] Field of Search ............... 378/86, 87, 88, 89, 378/145, 147, 149, 148

[56] References Cited

U.S. PATENT DOCUMENTS

| | | | |
|---|---|---|---|
| 4,480,332 | 10/1984 | Strecker | 378/87 |
| 4,785,401 | 11/1988 | Harding et al. | 378/88 |
| 4,956,856 | 9/1990 | Harding | 378/86 |
| 5,007,072 | 4/1991 | Jenkins et al. | 378/88 |
| 5,008,911 | 4/1991 | Harding | 378/86 |

FOREIGN PATENT DOCUMENTS 0360347  3/1990  European Pat. Off. .
2003753  9/1970  Fed. Rep. of Germany .

Primary Examiner—David P. Porta
Attorney, Agent, or Firm—Jack D. Slobod

[57] ABSTRACT

A first diaphragm arrangement is between a polychromatic X-ray radiator and an examination region for passing a primary radiation beam traversing the examination region on the generated surface of a cone. A detector arrangement comprising several detector elements receives radiation passed by the first diaphragm arrangement and a second diaphragm arrangement, which is located between the examination region and the detector arrangement and assigns to each respective detector element the scattered radiation which is scattered in a part of the primary radiation beam at a given scattering angle. The association between the individual sections of the primary radiation beam and the different detector elements is such that the second diaphragm arrangement has a slot-shaped opening and the shape of the slot-shaped opening and of the detector elements is adapted to the shape of a cross-section of the primary radiation beam.

33 Claims, 7 Drawing Sheets

|    | S1 | S2 | S3 | S4 | S5 | S6 | S7 |
|----|----|----|----|----|----|----|----|
| 1  |    |    |    | L  | I  | F  | C  |
| 2  |    |    |    | K  | H  | E  | B  |
| 3  |    |    |    | J  | G  | D  | A  |
| 4  |    |    | L  | I  | F  | C  |    |
| 5  |    |    | K  | H  | E  | B  |    |
| 6  |    |    | J  | G  | D  | A  |    |
| 7  |    | L  | I  | F  | C  |    |    |
| 8  |    | K  | H  | E  | B  |    |    |
| 9  |    | J  | G  | D  | A  |    |    |
| 10 | L  | I  | F  | C  |    |    |    |
| 11 | K  | H  | E  | B  |    |    |    |
| 12 | J  | G  | D  | A  |    |    |    |

ARRANGEMENT FOR MEASURING THE PULSE TRANSMISSION SPECTRUM OF X-RAY QUANTA

FIELD OF THE INVENTION

The invention relates to an arrangement for measuring the pulse transmission spectrum of X-ray quanta elastically scattered in an examination region comprising an X-ray radiator, a primary diaphragm arrangement arranged between the X-ray radiator and the examination region for diaphragming out a primary radiation beam traversing the examination region on the generated surface of a cone, a detector arrangement consisting of several detector elements and a secondary diaphragm arrangement, which is located between the examination region and the detector arrangement and assigns each time to the different detector elements the elastically scattered radiation of sections located at different depths of the examination region.

BACKGROUND OF THE INVENTION

Of interest is commonly owned copending application Ser. No. 821,511 entitled "X-ray Apparatus" filed Jan. 15, 1992 in the name of G. Harding et al.

Such an arrangement is known from EP-OS 360 347 corresponding to U.S. Pat. No. 5,008,911 incorporated by reference herein. It can be used for luggage control in order to identify, for example, explosives or drugs. In fact it has been found that these substances show on account of their crystalline structure a spectrum produced by diffraction and having distinctly pronounced peaks, which is characteristic of these substances and can be clearly distinguished from the spectra of other substances, which are generally taken along in pieces of luggage.

In the known arrangement, in which the diaphragm arrangement has a circular opening, so that the primary beam of radiation in the examination region generates the surface of a circular cone, the second diaphragm arrangement comprises several tubes, which are arranged concentrically to each other and through which the detector arrangement comprising several annular detector elements is struck by scattered radiation. As a result, the examination region is subdivided into a number of sections (in the form of parallel disks) corresponding to the number of the detector elements; each detector element detects the scattered radiation for one of these sections.

SUMMARY OF THE INVENTION

The invention has for its object to provide a arrangement of the kind mentioned in the opening paragraph, by means of which the pulse transmission spectrum can be determined in a different manner. According to the invention, this object is achieved in that the secondary diaphragm arrangement has a slot-shaped aperture and in that the slot-shaped aperture and the detector elements extend in the form of the arc of a circle around a system axis passing through the radiator.

The invention is based on the idea that the different sections of the primary beam of radiation in the examination region are imaged through the slot-shaped aperture of the secondary diaphragm arrangement in the form of a slot diaphragm on the detector arrangement so that the scattered radiation from different sections of the examination region is separately measured by the detector elements. The slot-shaped aperture (in a surface absorbing the radiation) of the secondary diaphragm arrangement therefore fulfils the same function as the gaps between the tubes of the known arrangement: also in this case, each detector element receives (through the aperture) scattered radiation at a practically constant scattering angle.

However, the scattered beams arriving from different sections of the examination region through the slot-shaped aperture at the different detector elements have different scattering angles—in contrast with the known arrangement, in which all detector elements are struck by scattered radiation scattered at the same scattering angle. For this reason and because the pulse transmission is proportional on good approximation to the product of scattering angle and energy of the X-ray quanta, for a given pulse transmission spectrum the energy of the X-ray quanta must be larger as the scattering angle is smaller.

An advantage of the invention in comparison with the known arrangement mentioned in the opening paragraph consists in that the secondary diaphragm arrangement according to the invention having a slot-shaped aperture can be much more readily manufactured with the required accuracy than the diaphragm consisting of coaxial tubes in the known arrangement. These tubes must in fact be comparatively long (for example 800 mm) with a diameter difference of at any rate a few mms and must extend coaxially to each other throughout the length, which requires a high mechanical precision.

The tubes in the known arrangement cannot be arbitrarily thin so that part of the scattered radiation is absorbed. Moreover, the tube walls act as a further source of scattered radiation. According to the invention, on the contrary, the scattered radiation is not reduced still further by the diaphragm arrangement and the scattered radiation additionally produced within the diaphragm arrangement (at the edges of the slot) is considerably weaker than in the known arrangement.

The more accurately the pulse transmission spectrum should be measured, the larger the number of the detector elements measuring independently of each other must be and the narrower the slot must be. However, this increase of measuring accuracy is connected with a lengthening of the measuring time, i.e. to the same extent as in the known arrangement. A preferred further embodiment permits, however, on the contrary a shortening of the measuring time and/or an increase of the measuring accuracy. This is achieved in that the secondary diaphragm arrangement has still further slot-shaped apertures, which extend in the form of the arc of a circle around the system axis and which are arranged so that at least part of the detector elements are struck by scattered radiation, which in further sections of the primary radiation beam is scattered at different scattering angles.

In this embodiment, a given section of the primary radiation beam within the examination region is "seen" not only by a single detector element, but also—through the further slot-shaped apertures—by other detectors, which is equivalent to the situation in which a detector element can "see" several relatively distant sections of the primary radiation cone. Thus, an increase of the measuring accuracy and/or a shortening of the measuring time can be attained. The fact that a detector element can then detect the scattered radiation from two or more mutually separated sections of the primary radiation cone means that the spectra of scattered radiation from these regions are superimposed on each other. In pieces of luggage, substances having a low density are usually taken along, which have a pulse transmission spectrum having a very large band width and without pronounced maxima. If one of these sections contains the substances of crystalline structure to be detected (explosive, drugs, etc.), these substances can be detected in spite of the superimposition on account of its pulse transmission spectrum having pronounced maxima characteristic thereof.

Only in a very small number of exceptional cases—if substances having a high density and/or a likewise crystalline structure are present in the examination region—wrong interpretations may be obtained. In order to avoid such wrong interpretations, it is ensured according to a further embodiment of the invention that means are provided for covering the further slot-shaped apertures.

If the further slot-shaped apertures are covered so that all detector elements receive scattered radiation only through the one slot-shaped aperture, each detector element "sees" only a single section of the primary radiation cone so that a perfect identification (with a lengthened measuring time) is possible.

According to a further embodiment of the invention, it is ensured that the primary radiation beam has the form of a flat fan, while in a further embodiment the system axis intersects the plane of the fan at an angle of 90° and the slot-shaped aperture and, as the case may be, further slot-shaped apertures extend in the form of a circle and with their longitudinal sides parallel to the fan. A flat fan can be considered as a sector of a circle, into which the generated surface of a cone is degenerated, whose (half) opening angle is 90°. The term "cone", over whose generated surface the primary radiation spreads, is therefore to be interpreted in a wide sense. The advantage of this further embodiment resides in the fact that for detecting the pulse transmission spectrum in a three-dimensional examination region only a unidimensional relative displacement (at right angles to the plane of the fan) is required between the primary radiation beam (fan) and the examination region in case the fan irradiates the whole examination region in the other direction.

According to another embodiment of the invention, it is ensured that the distance between the detector elements (and their width) increases with increasing distance from the primary radiation beam and that the secondary diaphragm arrangement is flat. The secondary diaphragm arrangement can then be constituted by a diaphragm plate.

In a further embodiment of the invention, it is ensured that several diaphragm positions relatively offset along the system axis are provided, that at least one secondary diaphragm arrangement is present and that a secondary diaphragm arrangement is each time in only one of the diaphragm positions. Thus, the searched substances, if they are present only in a thin layer, can be demonstrated more clearly.

The closer the position of the secondary diaphragm arrangement is to the examination region, the smaller is the size of the sections of the examination region detected by individual detector elements. As a result, the influence of a thin layer of the substance to be demonstrated on the pulse transmission spectrum increases. Therefore, a kind of "zoom effect" is obtained here. Moreover, the inaccuracy determined by the geometry of the arrangement with which the X-ray quantum demonstrated can be defined and which results in a spread of the spectral lines in the pulse spectrum also decreases when the distance between the second diaphragm arrangement and the examination region decreases. The diffraction pattern represented by the pulse transmission spectrum therefore becomes sharper.

BRIEF DESCRIPTION OF THE DRAWING

The invention will now be described more fully with reference to the accompanying drawings, in which.

DESCRIPTION OF THE PREFERRED EMBODIMENTS

Figure 1:
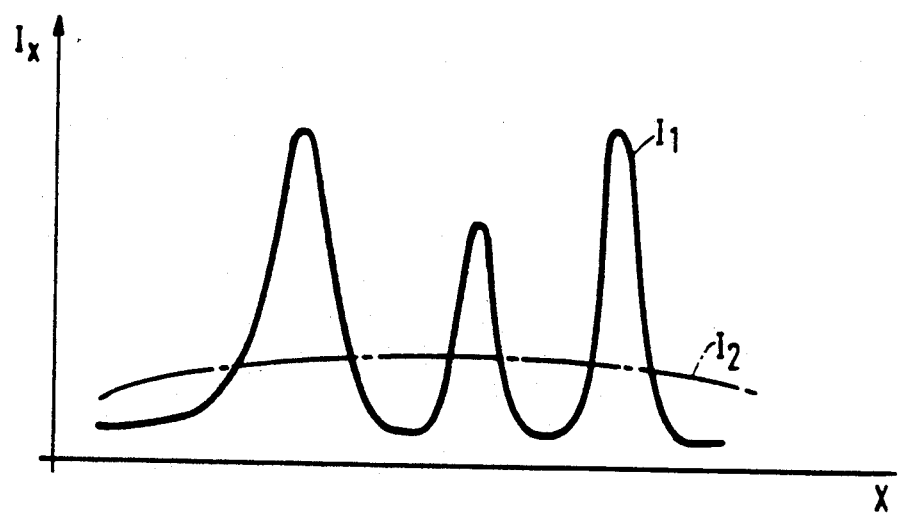
FIG. 1 shows the pulse transmission spectra of two different substances.

FIG. 1 shows a pulse transmission spectrum, i.e. the intensity $I_x$ of a radiation as a function of the pulse transmission for different substances. I1 designates the pulse transmission spectrum of a crystalline substance. With reference to this spectrum, the substance can consequently be identified. I2 designates the spectrum of a non-crystalline substance. It has a very large band width and exhibits no pronounced maxima, as I1.

Figure 2:
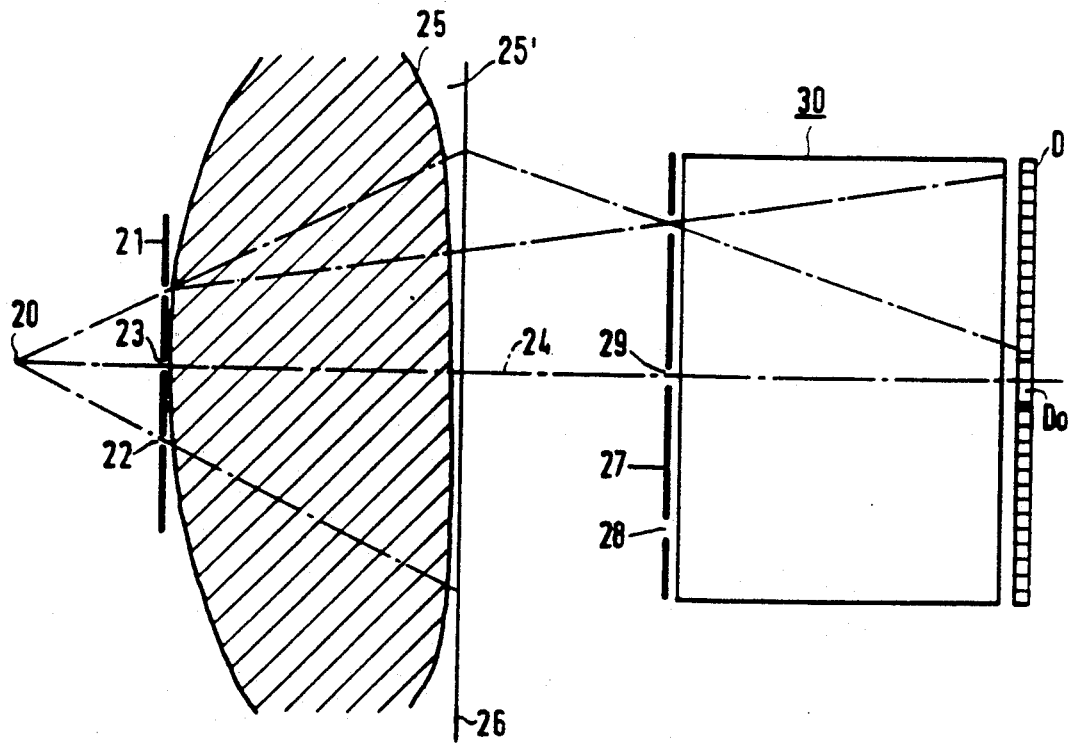
FIG. 2 shows a first embodiment of the invention.

The embodiment shown in FIG. 2 is not drawn to scale. The dimensions in the horizontal direction are enlarged in comparison with those in the vertical direction by a factor of more than ten.

Reference numeral 20 designates the focus of a polychromatic X-ray radiation source. The latter is generally constituted by an X-ray tube, which has an anode, in whose focus polychromatic radiation (stray radiation) is produced during electron bombardment. The anode is coated at least in part with a metal, preferably thorium, whose atomic number is higher than 80. On this broadband emission spectrum is generally superimposed the characteristic emission spectrum, which is determined by the anode material. The latter can adversely affect the evaluation if it originates from a tungsten anode. The characteristic lines of tungsten in fact lie at approximately 60 and 70 keV—in the middle of the energy range relevant for the evaluation—and are strongly pronounced at a tube voltage of, for example, 160 kV. If on the contrary an anode is used which is coated with a metal having a high atomic number, preferably thorium, at the edge of the relevant energy range—at approximately 110 keV—lines are obtained which are pronounced only weakly at a tube voltage of 160 kV.

The X-ray radiation is incident on a diaphragm 21 having a slot 22 in the form of a circular ring so that a primary beam of radiation is passed through the diaphragm plate 21 on the generated surface of a truncated cone. Because the diaphragm 21 transmits primary radiation, it is designated here also as primary diaphragm arrangement. The (half) opening angle of the primary beam of radiation source in radians is 0.041 rad at a distance between radiator 20 and diaphragm 21 of, for example, 745 mm. The diaphragm 21 is moreover provided with a hole 23, which is located at the center of the circular slot 22 and therefore passes a central beam a long axis 24, which also traverses the examination region and constitutes the axis of symmetry of the arrangement. The axis of symmetry constitutes the system axis 24 so that the central beam, the axis of symmetry and the system axis coincide in the present case. The examination region 25' in which the object 25 to be examined, for example a trunk, is situated, is limited on the opposite side by the diaphragm 21 and on the side remote from the radiator 20 by an x-ray radiation transparent plate 26, which extends parallel to the diaphragm 21 and is located at a distance therefrom of, for example 450 mm.

For detecting the scattered radiation produced by the primary beam of radiation in the examination region, a detector arrangement D is provided having a number of annular detector elements arranged concentrically to the axis 24. One of the detector elements is assigned to each section on the primary beam of radiation within the examination region 25' defined by a second diaphragm 27, which is located between the plate 26 and the detector arrangement D and which is designated hereinafter also as secondary diaphragm arrangement. The diaphragm 27 is provided for this purpose with a circular slot 28 concentric to the central beam on axis 24 and moreover has a central bore 29 for the passage of the primary beam on axis 24, which beam is sensed by and is measured by the central detector element $D_o$.

The assignment by the diaphragm slot determines that the innermost detector element $D_o$ is struck by scattered quanta, which enclose with the direction of the primary beam producing them a larger scattering angle (0.068 rad) than the scattered radiation reaching the outermost detector element (0.039 rad). If the fact is taken into account that the pulse transmission is proportional on good approximation to the product of the scattering angle and the energy of the scattered X-ray quanta, it follows therefrom that for determining a given range of the pulse transmission spectrum scattered quanta from a higher energy range are determinative of the sections of the examination region adjacent to the diaphragm 21 than those determinative of the sections adjacent to the plate 26. In order to detect the pulse transmission range between 0.8/nm and 1.8/nm, the smallest quantum energy is 30 keV (at the largest scattering angle) and the largest quantum energy is 115 keV (at the smallest scattering angle). A stray radiation spectrum having this energy distribution requires an operating voltage of at least 150 kV for the X-ray tube.

In order that the pulse transmission spectrum can be determined as accurately as possible, the scattering angle enclosed by the scattered radiation detected by a detector element with the primary beam, must be defined as accurately as possible. Therefore, as is explained also in EP-OS 360 347 (U.S. Pat. No. 5,008,911) with reference to FIG. 4b, therein only scattered radiation may be recorded with which the scattered beam, the primary beam producing it and the central beam are located in one plane or in a flat layer containing the primary beam on axis 24. For this purpose, a collimator 30, FIG. 2 in the present application comprising a number of lamellae located in radial planes is provided between the diaphragm 27 and the detector arrangement D. The collimator 30 may be arranged—instead of in the region between the detector arrangement D and the secondary diaphragm arrangement 27—also in the region between the detector arrangement and the plate 26, or such a collimator may be situated in each of these two regions.

Figure 3:
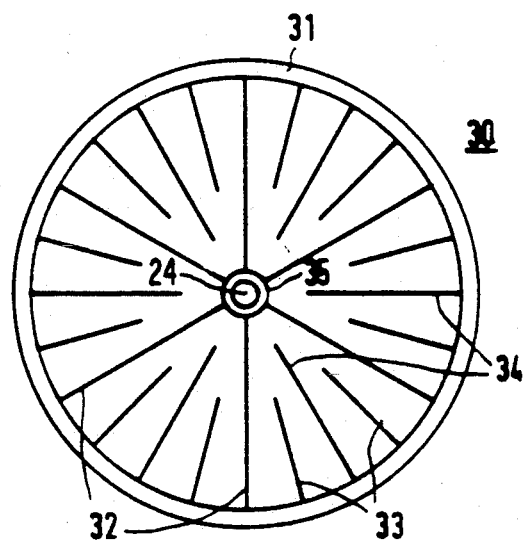
FIG. 3 shows a collimator used in the arrangement shown in FIG. 2.

The lamellae of the collimator 30 shown more fully in FIG. 3 must be comparatively thin (for example 0.5 mm), in order to suppress the smallest possible quantity of that scattered radiation which passes accurately in the planes of the lamellae. On the other hand, in dependence upon the geometric conditions, the lamellae must have a length lying between 1 m and 2 m. If laminated cores should be used as lamellae, the latter would be very flexible and would bend under their own weight and shadow the detector arrangement.

According to the invention, the lamellae therefore consist of a ceramic material which either comprises a heavy metal or is coated at its outer surfaces with a heavy metal, for example with a silver layer having a thickness of 50 $\mu$m. Normally, such thin silver layers are not sufficient to absorb X-ray radiation having an energy of, for example, 100 keV. However, since the scattered radiation strikes the lamellae at very small angles of incidence or since it must pass several lamellae if it is incident at a larger angle before it reaches the detector, the thickness is quite sufficient for absorption.

According to FIG. 3, the collimator 30 shown therein in plan view has a first part comprising a ceramic body comprising a hollow cylinder 35, through which the central beam on axis 24 can pass and which has on the outer side lamellae 32 regularly distributed along the periphery and extending radially. The second part of the collimator consists of a ceramic body, which has a tube 31 enclosing the tube 35 and the lamellae 32 and having inwardly directed lamellae 33 and 34 relatively offset periodically along its periphery. For the sake of clarity, FIG. 2 shows of the collimator parts only the outer contour of the second part. The first part is inserted after its manufacture into the second part, the second part having grooves (not shown) for the lamellae 32 so that the two collimator bodies occupy a defined position with respect to each other.

While the lamellae 32 fill the entire space between the hollow cylinders 31 and 35, the lamellae 33 arranged on either side at the lamellae 32 extend only over half the radial distance. The lamellae 34 located halfway between two lamellae 32 or between lamellae 33 have in the radial direction a dimension corresponding to the arithmetic average value of the dimensions of the lamellae 32 and 33. As the case may be, it may be efficacious that the thickness of the lamellae increases towards the outside.

The collimator 30 may be subdivided in the longitudinal direction (axis 24) and may consist of several modules (having a length of, for example, 200 mm), whose end faces are connected to each other in a suitable manner (for example by plugging). Each module may be manufactured by a sintering process.

Figure 4:
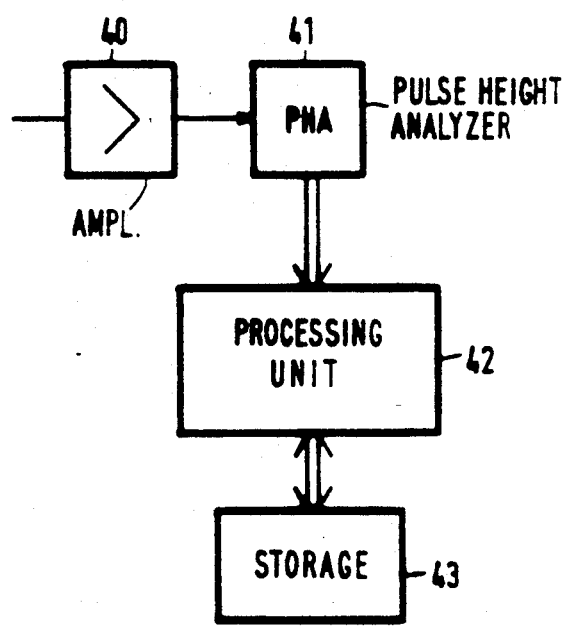
FIG. 4 shows the electronic system for evaluating the detector signals.

FIG. 4 shows the electronic system coupled to the detector elements for determining the pulse transmission spectrum from the measured elastically scattered X-ray radiation. It practically corresponds to the circuit described in EP-OS 360 347, (U.S. Pat. No. 5,008,911). It should only be noted here that the signals, which are delivered by the individual detector elements (for example of germanium) and whose amplitude is proportional to the energy of the measured quanta, are supplied through an amplifier 40 to a pulse height analyzer 41, which assigns to each output pulse produced by the associated detector element a digital data word, which is characteristic of the energy of the X-ray quantum. In the processing unit 42, the pulses from the various energy ranges are counted so that an energy spectrum of the X-ray quanta is obtained. The latter is standardized for the intensity of the primary radiation beyond the examination region (for this purpose the central beam along axis 24 is measured by the detector element $D_o$) so that an independence of the absorption of the radiation in the examination region is obtained.

After further disturbing effects have been eliminated in known manner, it is possible to determine from the variation of the intensity as a function of the energy with the scattering angle known for each detector element the intensity as a function of the pulse transmission (pulse transmission spectrum). This pulse transmission spectrum is compared in the unit 42, which can comprise a microprocessor, with the pulse transmission spectra of the substances to be detected, which are stored in the storage 43. When the measured spectrum corresponds to any of the stored spectra, this is indicated in a suitable manner.

The accuracy with which the pulse transmission spectrum can be determined depends not only upon the energy resolving power of the detector elements, but in the first instance upon the accuracy with which a given scattering angle can be assigned to a given detector element. This accuracy is in turn determined not only by the dimensions of the detector elements, but also by the slot-shaped opening 28 in the diaphragm 27, FIG. 2. The narrower this opening, the narrower is the scattering angle range assigned to a given detector element and the more accurate is the determination of the pulse transmission of the spectrum. On the other hand, the measuring time is longer, the narrower the slot, or the higher the measuring accuracy. So far the conditions correspond to those in the arrangement according to EP-OS 360 347 (U.S. Pat. No. 5,008,911).

Figure 5:
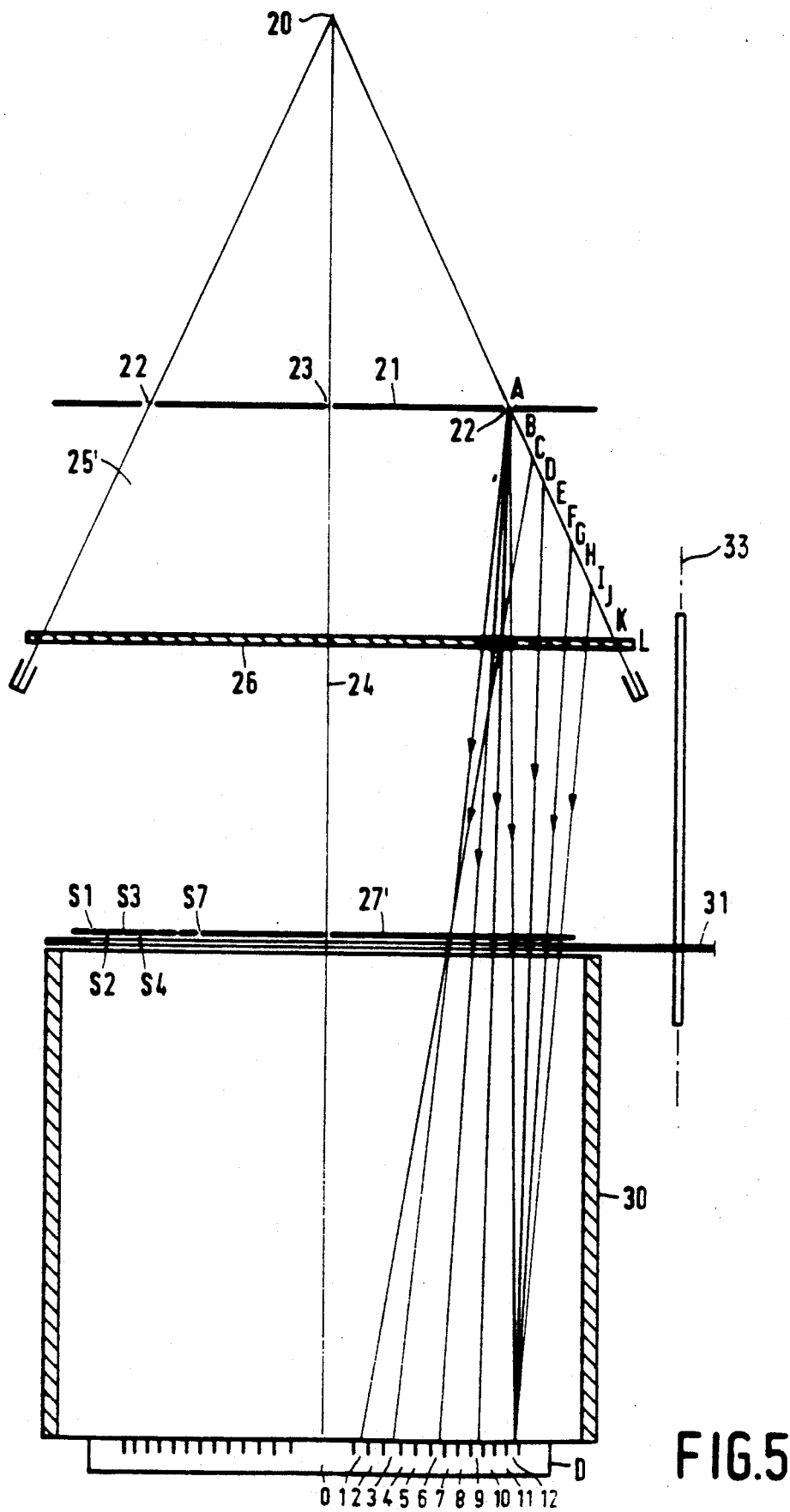
FIG. 5 shows an improved embodiment.

FIG. 5 shows a preferred embodiment, which in comparison with the arrangement of FIG. 2 yields a higher measuring accuracy and shorter measuring times, respectively. The same components are designated by like reference symbols. The collimator 30, which is likewise required for limiting the scattering angle, has the same construction as described with reference to FIG. 3.

The main difference with respect to the arrangement of FIG. 2 consists in that the secondary diaphragm 27' is provided with seven annular slots S1 ... S7 concentric to the central beam or axis 24. The central slot S4 of slots S1 ... S7 fulfils the same function as the slot 28 in the arrangement shown in FIG. 2: through this slot, each of the 12 detector elements 1 ... 12 "sees" one of twelve sections A ... L of the primary radiation beam in the examination region 25'. Besides, however, scattered radiation also penetrates from other sections to the detector elements, or each detector element "sees" through the remaining slots still other sections. As indicated by the connection lines, for example, scattered radiation from the section A reaches the detector elements 3, 6, 9 and 12 (through the respective slots S7, S6, S5 and S4), and likewise the detector element 12 "sees" besides the section A (through S4) the sections D, G and J (through S5, ... S7). In FIG. 5, only a fraction of the possible connection paths is shown.

Figures 6, 7:
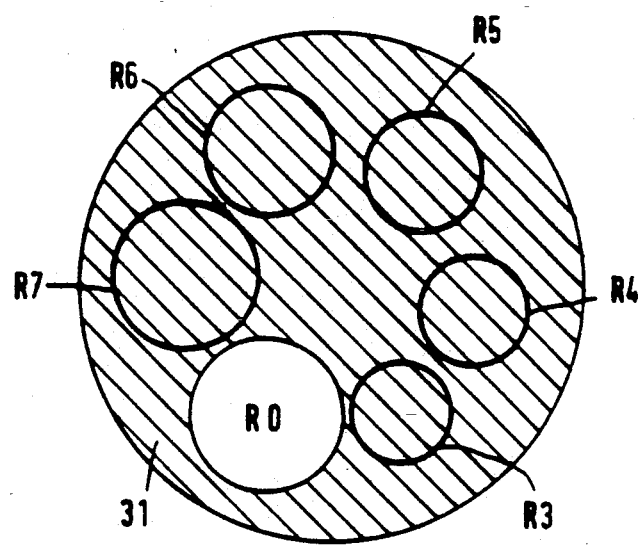
FIG. 6 shows a radiation matrix then present between the different sections of the examination region and the individual detector elements.
FIG. 7 is a plan view of rotatable diaphragm disk for use in the embodiment of FIG. 5.

The whole of these paths appears from the matrix representation according to FIG. 6, from which it is derived, for example, that the detector element 1 "sees" through the slot S4 the section L. It is seen in this representation that each detector element can receive scattered radiation from four different sections and that the sections whose scattered radiation commonly strikes a detector element are cyclically repeated. For example, the sections, L, I, F, C are "seen" by each of the detector elements 1, 4, 7, 10, while the sections K, H, E, B are "seen" by the detector elements 2, 5, 8 and 11. Through adjacent slots (for example S5 and S6), each detector element "sees" sections (for example A and D), between which each time two sections are located, for example C and B between A and D. The scattering angle difference between the scattered beams arriving at a detector element is therefore sufficiently great to permit a resolution of the diffraction lines, even if the same material is responsible for the scattered radiation. For these reasons, for the arrangement shown in FIG. 5, the sensitivity is therefore four times higher than for the arrangement shown in FIG. 2.

A dimensioning example for the arrangement shown in FIG. 5 will now be given. The sides facing the examination region 25' of the primary diaphragm 21 and of the plate 26 transparent to the X-ray radiation are located at a distance from the radiation source 20 of 744 and 1194 mm, respectively. The diameter of the slot-shaped circular opening 22 in the primary diaphragm 21 is chosen so that the primary radiation beam passed thereby encloses with the system axis 24, which in this case coincides with the central beam, an angle of 0.041 rad (the fact that this angle seems to be considerably larger in FIG. 5 is due to the imaging measure being considerably smaller in the vertical direction than in the horizontal direction). The detector elements D are located at a distance from the radiation source of 2744 mm. The average diameters of the first, the fifth and twelfth detector ring are 6.61 mm, 17.46 mm and 33.84 mm, respectively. The width of the detector rings linearly decreases from the inside to the outside, the width of the innermost detector ring being 2.289 mm and the width of the outermost detector ring being 1.701 mm.

The slot-shaped openings S1 ... S7 in the secondary diaphragm arrangement 27' have a width of 0.9 mm. The average radii of the slots S1 ... S7 are 21.62 mm, 25.60 mm, 29.28 mm, 32.66 mm, 35.78 mm, 38.67 mm and 41.32 mm. In the starting position of the diaphragm 27 shown in FIG. 1—i.e. the position in which each of the twelve detector elements detects through the slot S4 the scattered radiation from one of the twelve examination regions A ... L of the examination region 25'—the secondary diaphragm 27' is located at a distance from the radiation source 20 of 1774.5 mm.

The signal processing can then be effected, as described hereinafter for the detector element 12, which is struck by scattered radiation from the sections A, D, G and J. The assigned scattering angles are designated by Ta, Td, Tg and Tj. The measured energy spectrum can be converted by calculation into the pulse transmission spectrum utilizing the formula $$x = c^* \sin(T/2)/l_o \tag{1}$$

c being a constant, $l_o$ being the wavelength of the scattered radiation and T being the respective scattering angle. Since there are four possible scattering angles for each detector element, it is first assumed that the scattered radiation as a whole originates from the section A, and the energy spectrum is converted into a pulse transmission spectrum, utilizing the equation (1) with the value $T = T_a$. This spectrum is compared either directly or after addition of the spectra of the detectors 3, 6 and 9 (calculated each time for the section A) with the spectra from a catalogue of spectra stored in the storage 43 (FIG. 4).

If the desired substance is in fact present in the section A, it is detected. Although in practice the spectra of other substances present, for example, in the sections D, G and J are superimposed on these spectra, this is generally not distributing because these spectra have the variation indicated in FIG. 1 by I2, while the typical spectrum (I1) of the searched substances is strongly pronounced.

If none of the searched substances is present in the section A, the process is repeated, the angles Td, Tg and Tj being utilized for the conversion of the energy spectrum into a pulse transmission spectrum according to equation (1). Subsequently, this process is repeated for the other detector elements and the other sections.

The principle illustrated with reference to FIG. 5 can be varied in different respects.

For example, it is possible that in the arrangement shown in FIG. 5 several detectors are omitted, which does not influence the function of the arrangement, but indeed influences the responsiveness thereof. As shown clearly, for example, in FIG. 6, the three first detector elements 1, 2, 3 and the three outermost detector elements 10, 11, 12 can be omitted. (In this case, the two outermost slots S1 and S7 also become superfluous). Nevertheless, each of the twelve detector sections A ... L is detected by two detector elements. Such an arrangement could therefore process the scattered radiation from the different sections of the primary radiation cone with half the number of detector elements and with half the measuring time as compared with an arrangement as shown in FIG. 2. On the other hand, in the arrangement shown in FIG. 5 it would be possible to provide externally and/or internally further detector elements so that there would no longer be a slot (as the slot S4 in FIG. 5) through which each detector element is struck by scattered radiation from one of the sections of the primary radiation cone. With this increased number of detector elements, a certain increase of the detection sensitivity would be attained.

In the embodiment shown in FIGS. 5 and 6, the scattered radiation from the third next section in the primary radiation beam (v=3) is incident through an adjacent slot on a detector element; for example, scattered radiation from the section D, which is the third next with respect to the section A correlated to slot S7, strikes the detector element 3 through the slot S6 adjacent to the slot S7. However, the slots could also be arranged so that scattered radiation from the fourth next section (v=4) or from the second next section (v=2) reaches the same detector element. In this case, the slots S1 and S7 could be omitted (with v=4), or four further slots could be added (with v=2). Each detector element then would "see" instead of four sections three sections (v=4) or six sections (v=2) so that the detection sensitivity would be correspondingly lower or higher.

The number z of sections or of detector elements must not necessarily be 12, as in the embodiment. However, this number should be divisible by v without a remainder (for example z=9 for v=3 or z=10 for v=5). The increase in sensitivity then is z/v if 2z/v−1 slots—are present—in the respective required position.

The shape of diaphragm 27 strongly depends upon the geometry of the detector elements. In the embodiment shown in FIG. 5, the diaphragm 27' is a flat plate. It is then required that the distance between adjacent detector elements or their width is proportional to the distance of the relevant detector element from the line of intersection defined by the primary radiation cone and the plane in which the detector D is located. The sections A ... L on the primary radiation cone then also have a width decreasing from the inside to the outside.

If on the contrary detector rings are used each having the same width, the second diaphragm arrangement must have a shape opening towards the examination region, the width of the sections on the primary radiation cone decreasing even more strongly from the inside to the outside. If on the contrary the arrangement is struck in such a manner that the sections on the primary radiation cone all have the same width, the diaphragm 27' must have the shape of a key opening towards the detectors, the width of the detector elements decreasing from the inside to the outside even more strongly than in the embodiment shown in FIG. 1.

Only in a few exceptional cases, i.e. if besides a small quantity of the searched substance large quantities of strongly scattering substances or polycrystalline substances are present in the examination region, the superimposition of the spectra from different sections can lead to wrong interpretations. These wrong interpretations can be suppressed in that all slots but for one slot are covered. In fact each detector element can then receive scattered radiation from one section only. The covering means required to this end are shown in FIG. 7. They can take the form of a rotatable disphragm disk 31, which is pivotable about an axis 33 (FIG. 5) parallel to the system axis 24 and which comprises a circular cut-out part R0 and a series of annular cut-out parts R3 ... R7. If, as shown in FIG. 5, the circular cut-out part R0 is located in the radiation path, scattered radiation can reach the detector elements through all slots S1 ... S7. If on the contrary one of the annular openings R3 ... R7 is located in the radiation path, which can be achieved by a rotation about the axis 33, scattered radiation can pass through only one of the openings S3 ... S7, while all the remaining slot-shaped openings are covered. Instead of a rotatable plate, a slide may also be used as covering means, which is provided with circular and annular cut-out parts and is displaced perpendicular to the system axis. Differently constructed covering means are also possible. It is only essential that they permit receiving the scattered radiation optionally from all slot-shaped openings S1 ... S7 or from only one of these openings.

If all sections A ... L should then be monitored simultaneously, the annular opening R4 must be located in the radiation path, through which opening only the scattered radiation traversing the slot S4 reaches the detector elements. The average width of one of the sections monitored by one of the twoelve detector elements is then 37.5 mm—with a depth of the whole examination region of 450 mm. If, however, such a section contains a layer of one of the substances to be demonstrated, whose thickness is small as compared with the average thickness of one section, the indication of this substance can still give rise to difficulties.

Figure 8:
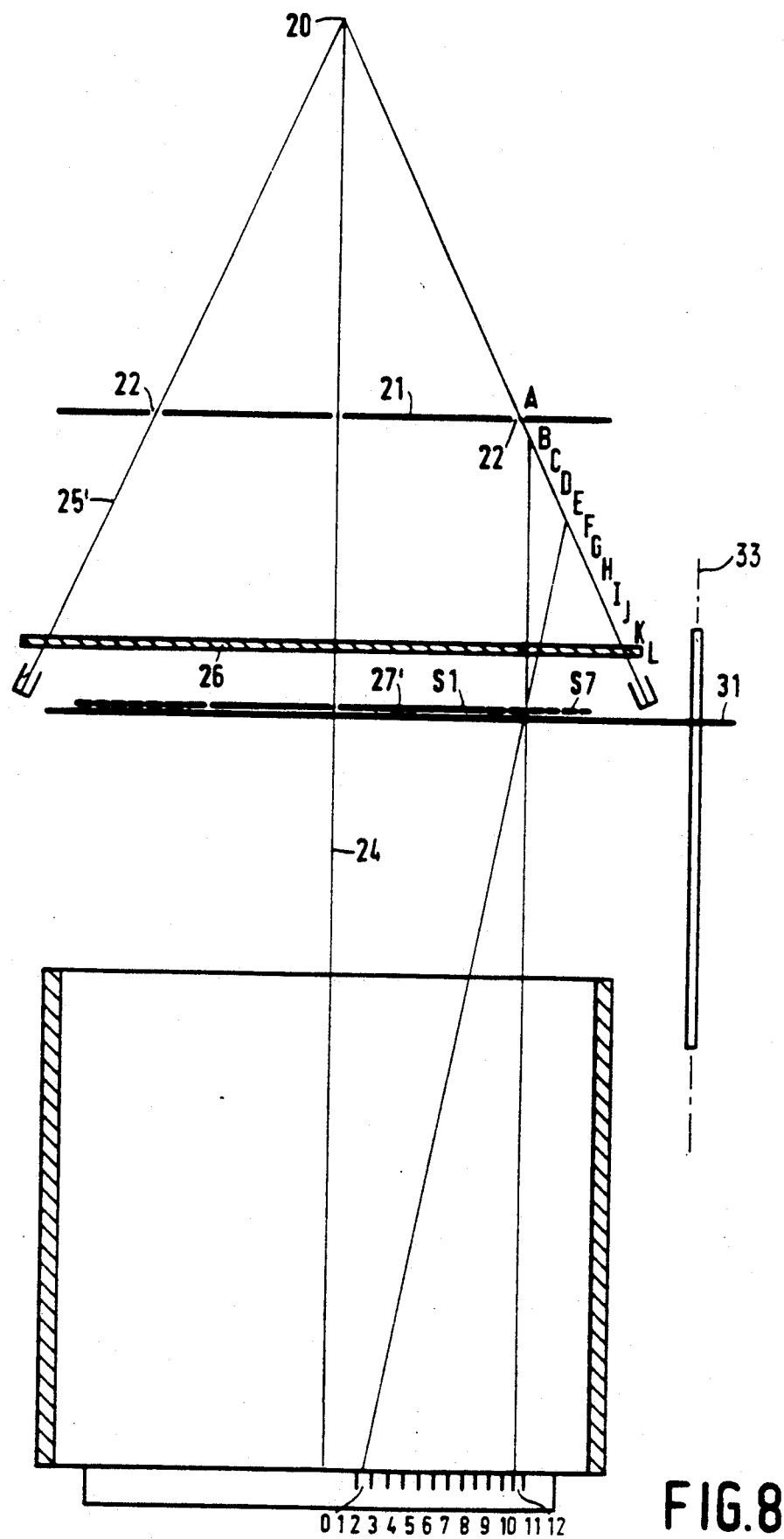
FIG. 8 shows the arrangement of FIG. 5, in which the secondary diaphragm arrangement is displaced towards the examination region.

These difficulties can be reduced in that the diaphragm 27' and the disk 31 are commonly displaced along the axis 33 towards the examination region. As shown by the representation of FIG. 8, the twelve detector elements can then no longer detect through the slot S4 all sections A . . . L of the primary radiation cone, but can detect only a central part thereof (i.e. the association of FIG. 6 between sections, slots and detector elements is then eliminated).

The chance shown of the geometry by displacement of the diaphragm 27 and disk 31 results in that the average thickness of a layer, which is detected each time by one of the twelve detector elements, decreases in the same ratio in which the region detected by the detector elements decreases (about 1:3). As a result, the indication of substances present in comparatively thin layers is facilitated. In addition, the inaccuracy given by the geometry of the arrangement when determining the scattering angle decreases if the slot-shaped opening S1 . . . S7 is located more closely to the examination region so that the pulse transmission spectrum can be defined with improved resolution ("more sharply").

FIG. 8 shows the secondary diaphragm 27' accordingly in a position, which lies in closer proximity to the examination region than the starting position of FIG. 5. When the distance (from the radiator source 20) has then decreased to about 1300 mm, only the second fifth (counted from the radiator source 20) can be detected through the slot S4. If other sections should be imaged, another slot must be uncovered. For imaging the sections A . . . C, for example, the disk 31 is pivoted so that the annular opening R3 is located in the radiation path, which uncovers only the slot S3. For monitoring the sections lying in closer proximity to the detectors, on the contrary, one of the annular openings R5 . . . R7 is pivoted into the radiation path. It is efficacious to displace the diaphragm 27' and disk 31 in the direction of the system axis 24 in such a manner that the ratio of the average distance of the detected part of the primary radiation cone from the secondary diaphragm arrangement to its distance from the detector elements remains approximately constant.

An examination can then be effected in the following manner. First the diaphragm 27' is brought into the position shown in FIG. 5 and the circular cut-out part RO of disk 31 is pivoted into the radiation path. All sections A to L can then be monitored, each by several detector elements. If none of the substances to be detected can be demonstrated, the diaphragm 27' is moved more closely to the examination region 25, the disk 31 being pivoted about the axis 33 so that in order of succession the annular sections R7 . . . R3 become operative, as a result of which the sections L . . . A are "zoomed" successively.

Instead of by means of a single diaphragm displaceable parallel to the system axis, the same effect may also be obtained in that in the various diaphragm positions a secondary diaphragm is provided at each position, one of which is moved perpendicular to the system axis 24 into the radiation path. Except for the diaphragm in the starting position, these other diaphragms must contain only one slot (with a different radius), while the width and the radius of the slots can be optimized.

In this embodiment, the collimator 30 with the fan-shaped lamellae can extend to the close proximity of the examination region 25' (only in the different diaphragm positions, a lateral inlet opening must be present for the secondary diaphragms), which has the advantage that the relative distance of the lamellae contained in the collimator 30 can be enlarged.

However, this solution has the disadvantage that for each diaphragm position a drive must be provided, which must move the associated diaphragm perpendicular to the system axis 24 into an exactly defined position. Therefore, this embodiment is relatively complicated.

In the embodiments described above, a rotation symmetry is given. However, essentially no symmetry is required; for example, there may also be worked with a primary radiation cone having a semi-circular cross-section if the slot or slots in the diaphragm 27' and the detector elements also have a semi-circular form. Likewise, it is not required that the cross-section of the primary radiation cone, the slots and the detector elements are of circular form. It generally holds that the primary radiation beam must spread in the examination region on the generated surface of a cone (or on a part of such a generated surface).

Figure 9:
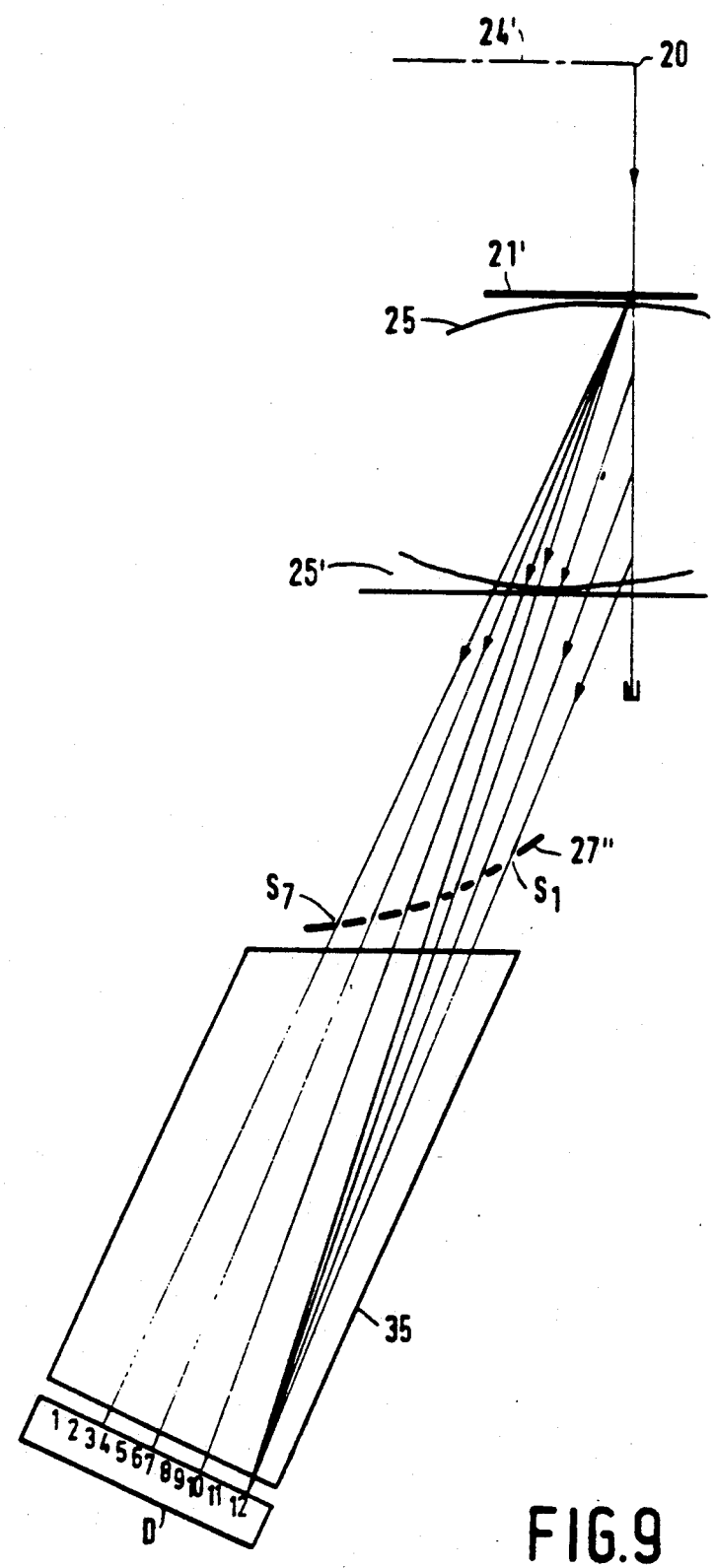
FIG. 9 shows another embodiment.
Figure 10:
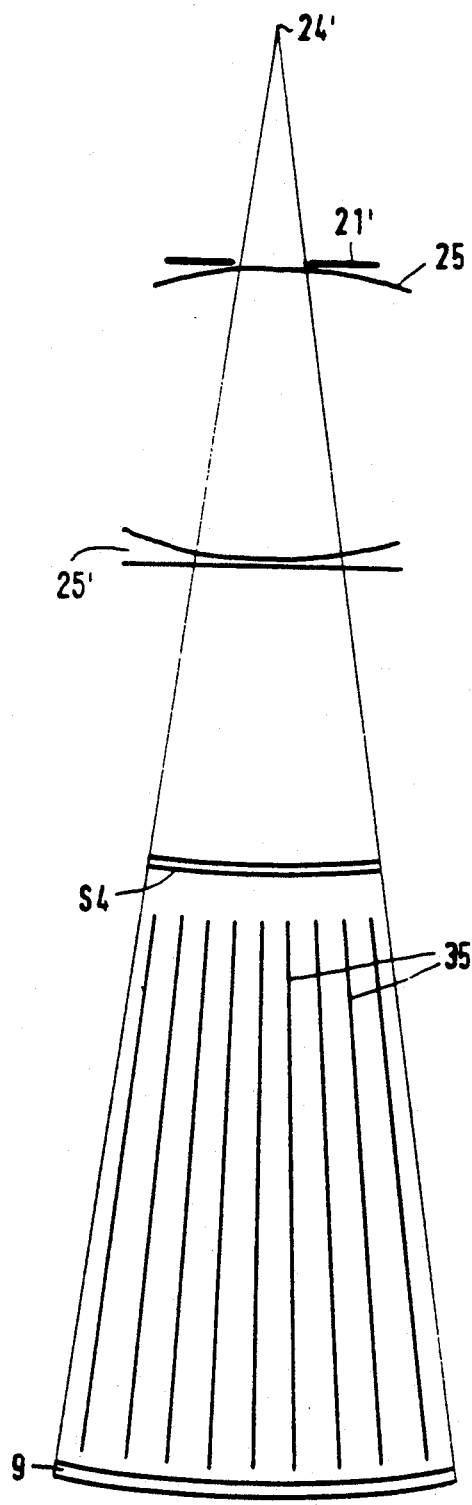
FIG. 10 shows the embodiment of FIG. 9 in an elevation rotated by 90°.

FIGS. 9 and 10 show an embodiment of the invention modified in this respect in two perspective views relatively offset by 90°. The primary radiation diaphragm 21' is provided with a rectilinear slot perpendicular to the plane of the drawing of FIG. 9 so that the examination region is traversed by a flat primary radiation fan beam. The system axis 24' passing through the focus source 20 is defined by flat lamellae 35 of radiation-absorbing material (FIG. 9 shows only one of these lamellae) between the examination region and the detector arrangement D. It corresponds to the common straight line of the sections of all planes of the lamellae and extends perpendicular to the primary radiation fan.

A curved diaphragm 27' having seven slot-shaped openings S1 . . . S7 is located between the examination region 25' and the detector D arrangement. The slot-shaped openings are each located in planes perpendicular to the system axis 24 and have the form of the arc of a circle curved around the system axis. The same applies to the detector elements 1 . . . 12. Since in practice a comparatively large arc cannot be realized by a single detector element, the detector elements may also be constituted by subdetector elements, which are relatively offset along the circumference and whose output signals are superimposed on each other. For the sake of clarity, in FIG. 9 the scattering angle, at which scattered radiation from the fan beam reaches the detector elements, is shown comparatively large. In fact, however, the angle is so large as indicated with reference to FIG. 2 so that the detector elements are mainly struck by elastically scattered X-ray radiation.

If a piece of luggage should be examined by means of the arrangements shown in FIGS. 2, 5 or 8, a bidimensional relative displacement between the radiation beam and the piece of luggage is required, while in equidistant of this bidimensional relative displacement the pulse transmission spectra at the different depths of the examination region must be determined. In the arrangement shown in FIG. 9, a uni-dimensional relative displacement (perpendicular to the plane of the radiation fan) can be sufficient if the opening angle of the fan-shaped radiation beam is sufficiently large to detect the whole piece of luggage. As a result, the examination is simplified and shortened.

I claim:

1. An arrangement for measuring the pulse transmission spectrum of X-ray quanta elastically scattered in an examination region comprising an X-ray radiator having a system axis passing therethrough, a primary diaphragm arrangement between the X-ray radiator and the examination region for passing a primary radiation beam traversing the examination region on a generated surface of a cone, a detector arrangement comprising a plurality of detector elements and a secondary diaphragm arrangement which is located between the examination region and the detector arrangement and which assigns to each of the different detector elements the elastically scattered radiation of sections located at different depths of the examination region, said primary and secondary diaphragm arrangements each having a slot-shaped opening, said slot-shaped openings and the detector elements extending in the form of an arc of a circle around said system axis, wherein the secondary diaphragm arrangement has further slot-shaped openings which extend in the form of an arc of a circle around the system axis and which are arranged so that at least a portion of the detector elements receives incident scattered radiation, which is scattered in further sections of the primary radiation cone at different scattering angles.

2. An arrangement as claimed in claim 1, including means for covering the further slot-shaped openings.

3. An arrangement as claimed in claim 2 wherein the slot-shaped openings of the secondary diaphragm arrangement, the cross-section of the primary radiation beam and the detector elements have a circular shape.

4. An arrangement as claimed in claim 1 including further slot-shaped openings in the secondary diaphragm arrangement wherein the slot-shaped openings of the secondary diaphragm arrangement, the cross-section of the primary radiation beam and the detector elements have a circular shape.

5. An arrangement as claimed in claim 1, wherein a relative distance between the detector elements increases with an increasing distance from the primary radiation beam, and wherein the secondary diaphragm arrangement is flat.

6. An arrangement as claimed in claim 5 wherein polychromatic X-ray radiation is emitted by said X-ray radiator, which has an anode which is coated at least in part with a metal, whose atomic number is higher than 80.

7. An arrangement as claimed in claim 1 wherein polychromatic X-ray radiation is emitted by said X-ray radiator, which has an anode which is coated at least in part with a metal whose atomic number is higher than 80.

8. An arrangement as claimed in claim 7 wherein several diaphragm positions are provided for at least one of said diaphragm arrangements, said positions being relatively offset along the system axis, at least one secondary diaphragm arrangement being present for each diaphragm position.

9. An arrangement as claimed in claim 8 wherein a single secondary diaphragm arrangement is present, which is displaceable relative to at least one of the examination region and the detector arrangement parallel to the system axis.

10. An arrangement as claimed in claim 9 including covering means displacable in common with the secondary diaphragm arrangement and displaceable in such a manner that for each displacement one of the slot-shaped openings in the secondary diaphragm arrangement is uncovered and the scattered radiation directed to the remaining openings is absorbed.

11. An arrangement as claimed in claim 10 wherein the covering means comprise a radiation-absorbing plate having several openings in the form of the arc of a circle, said covering means being adapted to the dimensions of the slot-shaped openings and one of which openings become operative in the radiation path by one of a translatory and rotary movement.

12. An arrangement as claimed in claim 1 wherein several diaphragm positions are provided for at least one of said diaphragm arrangements, said positions being relatively offset along the system axis, at least one secondary diaphragm arrangement being present for each diaphragm position.

13. An arrangement as claimed in claim 12 wherein a single secondary diaphragm arrangement is present, which is displaceable relative to at least one of the examination region and the detector arrangement parallel to the system axis.

14. An arrangement as claimed in claim 13, including covering means which can be displaced in common with the secondary diaphragm arrangement and are displaceable in such a manner that for each displacement one of the slot-shaped openings in the secondary diaphragm arrangement is uncovered and the scattered radiation directed to the remaining openings is absorbed.

15. An arrangement as claimed in claim 14 wherein the covering means comprise a radiation-absorbing plate having several openings in the form of the arc of a circle, said covering means being adapted to the dimensions of the slot-shaped openings and one of which openings becomes operative in the radiation path by one of a translatory and rotary movement.

16. An arrangement as claimed in claim 15 wherein a collimator arrangement is between the examination region and the detector arrangement, which collimator arrangement comprises lamellae which adsorb the scattered radiation and which lamellae are each located in a plane containing the system axis.

17. An arrangement as claimed in claim 16 wherein the lamellae comprise a ceramic material provided with one of a layer of heavy metal and a material containing a heavy metal.

18. An arrangement as claimed in claim 17 wherein the lamellae have different dimensions in a direction perpendicular to the system axis so that the space between the lamellae varies to the smallest possible extent as a function of the distance from the system axis.

19. An arrangement as claimed in claim 1 wherein a collimator arrangement is between the examination region and the detector arrangement, which collimator arrangement comprises lamellae which absorb the scattered radiation and which lamellae are each located in a plane containing the system axis.

20. An arrangement as claimed in claim 19, wherein the lamellae comprise a ceramic material provided with one of a layer of heavy metal or containing a heavy metal.

21. An arrangement as claimed in claim 19, wherein the lamellae have different dimensions in a direction perpendicular to the system axis so that the space between the lamellae varies to the smallest possible extent as a function of the distance from the system axis.

22. An arrangement for measuring the pulse transmission spectrum of X-ray quanta elastically scattered in an examination region comprising:

an X-ray radiator having a system axis passing therethrough;

a primary diaphragm arrangement between the X-ray radiator and the examination region for passing a primary radiation beam traversing the examination region;

a detector arrangement comprising a plurality of detector elements;

a secondary diaphragm arrangement located between the examination region and the detector arrangement and which assigns to each of the different detector elements the elastically scattered radiation of sections located at different depths of the examination region;

said primary and secondary diaphragm arrangements each having a slot-shaped opening, said slot-shaped openings of the secondary diaphragm arrangement and the detector elements extending in the form of an arc around said system axis; and means for forming said primary radiation beam into a relatively flat fan-shaped beam.

23. An arrangement as claimed in claim 22, wherein the system axis intersects the plane of the fan at an angle of 90°.

24. An arrangement as claimed in claim 23 wherein the relative distance between the detector elements increases with an increasing distance from the primary radiation beam and the secondary diaphragm arrangement is flat.

25. An arrangement as claimed in claim 22 wherein the relative distance between the detector elements increases with an increasing distance from the primary radiation beam and the secondary diaphragm arrangement is flat.

26. An arrangement as claimed in claim 25 wherein polychromatic X-ray radiation is emitted by said X-ray radiator, which has an anode which is coated at least in part with a metal whose atomic number is higher than 80.

27. An arrangement as claimed in claim 26 wherein several diaphragm positions are provided for at least one of said diaphragm arrangements, said positions being relatively offset along the system axis, at least one secondary diaphragm arrangement being present for each diaphragm position.

28. An arrangement as claimed in claim 27 wherein a single secondary diaphragm arrangement is present, which is displaceable relative to at least one of the examination region and the detector arrangement parallel to the system axis.

29. An arrangement as claimed in claim 28 including covering means which can be displaced in common with the secondary diaphragm arrangement and are displaceable in such a manner that for each displacement one of the slot-shaped openings in the secondary diaphragm arrangement is uncovered and the scattered radiation directed to the remaining openings is absorbed.

30. An arrangement as claimed in claim 29 wherein the covering means comprise a radiation-absorbing plate having several openings in the form of the arc of a circle, said covering means being adapted to the dimensions of the slot-shaped openings and one of which openings becomes operative in the radiation path by one of a translatory and rotary movement.

31. An arrangement as claimed in claim 30 wherein a collimator arrangement is arranged between the examination region and the detector arrangement, said collimator arrangement comprising lamellae which absorb the scattered radiation, said lamellae being each located in a plane containing the system axis.

32. An arrangement as claimed in claim 31 wherein the lamellae comprise a ceramic material provided with one of a layer of heavy metal and a material containing a heavy metal.

33. An arrangement as claimed in claim 32 wherein the lamellae have different dimensions in a direction perpendicular to the system axis so that the space between the lamellae varies to the smallest possible extent as a function of the distance from the system axis.

* * * * *